(12) United States Patent
Moscherosch

(10) Patent No.: US 6,468,517 B2
(45) Date of Patent: *Oct. 22, 2002

(54) ODOR CONTROL IN ABSORBENT ARTICLES

(75) Inventor: Michael Moscherosch, Doylestown, PA (US)

(73) Assignee: McNeil-PPC, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/409,528

(22) Filed: Sep. 30, 1999

(65) Prior Publication Data

US 2002/0018761 A1 Feb. 14, 2002

(51) Int. Cl.⁷ .............................. A61L 9/00; A61K 9/00; A61N 25/34; A61F 13/15
(52) U.S. Cl. ..................... 424/76.1; 424/400; 424/402; 604/358; 604/359
(58) Field of Search ................................ 604/358, 359; 424/76.1, 402, 400, 443

(56) References Cited

U.S. PATENT DOCUMENTS

| | | | |
|---|---|---|---|
| 4,186,743 A | | 2/1980 | Steiger |
| 4,247,526 A | * | 1/1981 | Jarvis et al. |
| 4,356,190 A | | 10/1982 | Kraskin |
| 5,037,412 A | * | 8/1991 | Tanzer et al. |
| 5,122,407 A | * | 6/1992 | Yeo et al. .................. 428/138 |
| 5,161,686 A | * | 11/1992 | Weber et al. ................ 206/440 |
| 5,306,487 A | | 4/1994 | Karapasha et al. |
| 5,567,231 A | | 10/1996 | Yokoo et al. |
| 5,733,272 A | | 3/1998 | Brunner et al. |
| 5,885,263 A | | 3/1999 | Gancet et al. |
| 5,944,704 A | * | 8/1999 | Guarracino et al. ......... 604/359 |
| 5,981,668 A | * | 11/1999 | Fujita et al. ............. 525/329.9 |
| 6,229,062 B1 | * | 5/2001 | Mandell et al. |

FOREIGN PATENT DOCUMENTS

| | | |
|---|---|---|
| EP | 0 392 528 A2 | 10/1990 |
| EP | 0 889 063 A | 1/1999 |
| GB | 769 799 A | 3/1957 |
| GB | 2 333 703 A | 8/1999 |
| JP | 06335614 | 12/1994 |
| WO | WO97/01317 | 1/1997 |
| WO | WO 00 66187 A | 11/2000 |

OTHER PUBLICATIONS

European Search Report for EP 00120955 dated Jun. 14, 2002.

Lee, TS et al., "Bacteriostatic Effect of Condensed Phosphate on the Growth of Bacteria" Bull Korean Fish Soc., vol. 21, No. 2, 1988 pp. 97–104 XP001071129.

Shults GW et al., "Flavor and Textural Changes in Radappertized Chickens as Affected by Irradiation Temperature Sodium Chloride and Phosphate Additions" Journal of Food Science, vol. 42, No. 4, 1977, pp. 885–889 XP001070739.

* cited by examiner

Primary Examiner—Thurman K. Page
Assistant Examiner—Amy E Pulliam

(57) ABSTRACT

A method of odor control in disposable, absorbent articles is provided using odor control additives comprising phosphorous-containing compounds.

15 Claims, No Drawings

ODOR CONTROL IN ABSORBENT ARTICLES

The present invention relates to odor control in disposable, absorbent articles using phosphorous-containing compounds.

BACKGROUND OF THE INVENTION

A variety of additives are currently used in disposable, absorbent articles for reducing or controlling malodors associated with body exudates. It is known that many malodors associated with body exudates are due to the microbial decomposition of lipids, particularly triglycerides and phospholipids, into fatty acids. U.S. Pat. No. 4,356,190, for example, discloses the use of compounds such as EDTA to inhibit the formation of such fatty acids. Other materials as diverse as zeolites, baking soda, compounds containing active carbon, and charcoal have also been employed in absorbent articles for odor control. See for instance, U.S. Pat. No. 5,306,487.

U.S. Pat. No. 5,567,231 relates to a deodorant comprising 5 to 100 weight % of a calcium phosphate compound having a Ca/P molar ratio of 0.8 to 2.0. Materials such as filter sheets incorporating such a compound are taught to have improved adsorptivity to a side variety of substances, such as oil-soluble substances, odor substances, viruses, etc.

Applicant has now discovered that malodors associated with the microbial decomposition of lipids in body exudates absorbent articles can be reduced or eliminated by incorporating into such absorbent articles an odor control additive comprising at least one water soluble salt containing an anion selected from the group consisting of $P^2O_7^{4-}$, $P_3O_9^{3-}$, and $P_3O_{10}^{5-}$. Alternatively, such odor control additive may comprise a water soluble compound of the formula $(APO_3)_n$, wherein A is a Group 1 element and n is 4 to 50.

SUMMARY OF THE INVENTION

The present invention provides a disposable, absorbent article comprising a liquid permeable cover and an absorbent core, wherein said absorbent article contains an odor control additive comprising at least one water soluble salt containing an anion selected from the group consisting of $P_2O_7^{4-}$, $P_3O_9^{3-}$, and $P_3O_{10}^{5-}$.

The present invention also provides a disposable, absorbent article comprising a liquid permeable cover and an absorbent core, wherein said absorbent article contains an odor control additive comprising a water soluble compound of the formula $(APO_3)_n$, wherein A is a Group 1 element and n is 4 to 50.

The present invention further provides methods of reducing malodors in a disposable, absorbent article, comprising incorporating into the absorbent article an odor control additive comprising at least one water soluble salt containing an anion selected from the group consisting of $P_2O_7^{4-}$, $P_3O_9^{3-}$, and $P_3O_{10}^{5}$, or a water soluble compound of the formula $(APO_3)_n$, wherein A is a Group 1 element and n is 4 to 50.

DETAILED DESCRIPTION OF THE INVENTION

The absorbent article may for example be a sanitary napkin, pantyliner, diaper, incontinence pad, interlabial article, tampon or other intravaginal device, shoe liner, or other similar product for absorbing exudates from the body, such as menses, urine, feces, or sweat. Preferably, the absorbent article is a sanitary napkin or a pantyliner. Such sanitary napkin or pantyliner may have an approximately rectangular, oval, dogbone, or peanut shape. Depending on the nature of the absorbent article, its size may vary. For example, sanitary napkins typically have a caliper of about 1.4 to about 5 mm, a length of about 3 to about 16 inches, and a width of about 1 to about 5 inches. Pantyliners typically have a caliper of less than about 0.2 inches, a length of less than about 8 inches, and a width of less than about 3 inches.

The absorbent article generally comprises in sequence from its body-facing surface to its garment-facing surface liquid permeable cover, an absorbent core, and optionally a backsheet. The cover of the absorbent article may be formed from any fluid pervious material that is comfortable against the skin and permits fluid to penetrate to the absorbent core, which retains the fluid. The cover should retain little or no fluid to provide a relatively dry surface, since its external surface forms the body-facing surface of the article. A variety of materials are known for preparing covers, and any of these may be used. For instance, the cover may be a fibrous non-woven fabric made of fibers or filaments of polymers such as polyethylene, polypropylene, polyester, or cellulose. Alternatively, the cover may be formed from an apertured polymeric film. The thickness of the cover may vary from approximately 0.001 to 0.062 inch, depending on the material chosen.

Generally, the cover is a single sheet of material having a width sufficient to form the body-facing surface of the article. The cover may be the same length, or optionally longer than the absorbent core so as to form transverse ends. Such transverse ends may be sealed with other layers to fully enclose the absorbent core.

The absorbent core may be comprised of a loosely associated absorbent hydrophilic material such as cellulose fibers, including wood pulp, regenerated cellulose fibers or cotton fibers, or other absorbent materials generally known in the art, including acrylic fibers, polyvinyl alcohol fibers, peat moss and superabsorbent polymers.

The absorbent article may further comprise a backsheet that is substantially or completely impermeable to liquids, the exterior of which forms the garment-facing surface of the article. The backsheet may comprise any thin, flexible, body fluid impermeable material such as a polymeric film, for example, polyethylene, polypropylene, or cellophane. Alternatively, the backsheet may be a normally fluid permeable material that has been treated to be impermeable, such as impregnated fluid repellent paper or non-woven fabric material, or a flexible foam, such as polyurethane or cross-linked polyethylene. The thickness of the backsheet when formed from a polymeric film typically is about 0.001 to 0.002 inch. A variety of materials are known in the art for use as backsheet, and any of these may be used.

Generally, the backsheet is a single sheet of material having a width sufficient to form the garment-facing surface of the absorbent article. The backsheet may extend around the sides of the absorbent core in a C-shaped configuration with the portions of the backsheet adjacent its longitudinal edges extending upwardly from the garment-facing surface toward the body-facing surface of the article. Preferably the backsheet is breathable, i.e., a film that is a barrier to liquids but permits gases to transpire. Materials for this purpose include microporous films in which microporosity is created by stretching an oriented film. Single or multiple layers of permeable films, fabrics, and combinations thereof that provide a tortuous path, and/or whose surface characteristics provide a liquid surface repellent to the penetration of liquids may also be used to provide a breathable backsheet.

The absorbent article may be applied to the crotch of underpants by placing the garment-facing surface of the absorbent article against the inside surface of the crotch of the underpants. Strips of pressure sensitive adhesive may be applied to the garment-facing surface of the absorbent article to help maintain it in place. As used herein, the term "pressure-sensitive adhesive" refers to any releasable adhesive or releasable tenacious means. Suitable pressure sensitive adhesives include for example water-based adhesives such as acrylate adhesives. Alternatively, the adhesive may comprise "hot melt" rubber adhesives or two-sided adhesive tape.

A paper release strip that has been coated on one side may be applied to protect the strips of adhesive prior to use. The coating, for example silicone, reduces adherence of the coated side of the release strip to the adhesive. The release strip can be formed from any suitable sheet-like material which, when coated, adheres with sufficient tenacity to the adhesive to remain in place prior to use but can be readily removed when the absorbent article is to be used.

The absorbent article may comprise other known materials, layers, and additives, such as transfer layers, foam layers, net-like layers, perfumes, medicaments, moisturizers, and the like, many examples of which are known in the art. The absorbent article can optionally be embossed with decorative designs using conventional techniques.

According to the invention, the absorbent article contains one or more odor control additives comprising one or more phosphorous-containing compounds of the following types: 1) water soluble salts containing an anion selected from the group consisting of $P_2O_7^{4-}$, $P_3O_9^{3-}$, and $P_3O_{10}^{5-}$; and 2) water soluble compounds of the formula $(APO_3)_n$, wherein A is a Group 1 element and n is 4 to 50. The water soluble salts containing an anion selected from the group consisting of $P_2O_7^{4-}$, $P_3O_9^{3-}$, and $P_3O_{10}^{5-}$ preferably comprise a cation containing a Group 1 element or ammonium. More preferably such water soluble salts comprise a cation containing sodium. Particularly preferred water soluble salts are tetrasodium pyrophosphate and pentasodium triphosphate.

In water soluble compounds of the formula $(APO_3)_n$, A is preferably sodium and n is preferably 4 to 50. More preferably n is 15 to 20.

In addition to the above phosphorous-containing compounds, the odor control additive may comprise other ingredients such as EDTA, zeolites, or other known odor control agents.

The odor control additive may by incorporated into or onto the cover, absorbent core, or backsheet of the absorbent article, or combinations thereof. Alternatively, if the absorbent article comprises additional layers, such as a transfer layer, etc., the odor control additive may be incorporated into or onto such additional layers. Preferably, the cover of the absorbent article comprises the odor control additive, so the odor control additive is in close proximity to the body and the site of initial discharge of body exudates.

The physical form of the odor control additive is not critical to the invention. The odor control additive may be used in the form of powder or a liquid solution. It may also be incorporated into one or more adhesives used in the absorbent article. See for example U.S. Pat. No. 4,186,743, which relates to the use of microcapsules containing a deodorant material that are contained in the adhesive element of a sanitary napkin.

The amount of odor control additive used in the absorbent article depends on the size and nature of the layer it is being incorporated into and the absorbent article.

Typically, the amount of odor control additive is used is to provide about 0.01 to about 1 gram of phosphorous-containing compound per square inch of layer. Preferably, about 0.02 to about 0.50 gram of phosphorous-containing compound per square inch of layer should be present in the absorbent article. However, even smaller amounts of odor control additive are capable of reducing malodor levels in the absorbent article.

It is believed the odor control additive helps to reduce malodors by interfering with the decomposition of lipids by bacteria into fatty acids in body exuadates. The odor control additive also has a somewhat basic pH and can therefore neutralize the fatty acids that are produced.

Advantageously, the phosphorous-containing compounds contained in the odor control additive are safe for contact with humans. They are also relatively less harmful to the environment than many other types of compounds. They are also less expensive than EDTA for example.

The following example is intended to illustrate the invention further.

EXAMPLE

A pantyliner is made according to the invention as follows. The pantyliner comprises a cover, an absorbent core, and a backsheet. The absorbent core is made of airlaid pulp. It is 35 mm wide, 150 mm long and 1.2 mm thick. The absorbent core also contains 0.1 gram of tetrasodium pyrophosphate as an odor control additive. The tetrasodium pyrophosphate is used in the form of a powder, and is evenly dispersed over the absorbent core.

I claim:

1. A disposable, absorbent article comprising a liquid permeable cover and an absorbent core, said absorbent article contains an odor control additive in an amount from about 0.1 to about 1 g. per square inch of layer, wherein the odor control additive is a water soluble salt containing an anion selected from the group consisting of $P_3O_9^{3-}$ and $P_3O_{10}^{5-}$ and a cation containing a Group 1 element or ammonium.

2. The disposable absorbent article of claim 1, wherein said Group 1 element is sodium.

3. The disposable article of claim 1, wherein said odor control additive comprises pentasodium triphosphate.

4. The disposable absorbent article of claim 1, wherein the cover comprises the odor control agent.

5. The disposable absorbent article of claim 1, wherein the absorbent core comprises the odor control agent.

6. The disposable absorbent article of claim 1 further comprising a backsheet and wherein the backsheet comprises the odor control agent.

7. A disposable, absorbent article comprising a liquid permeable cover, and an absorbent core, wherein said absorbent article contains an odor control additive comprising a water soluble compound of the formula $(APO_3)_n$, wherein A is a Group 1 element and n is 4 to 50.

8. The disposable absorbent article of claim 7, wherein said Group 1 element is sodium, and n is 15 to 20.

9. A method of reducing malodors in a disposable, absorbent article, comprising incorporating an odor control additive in an amount from about 0.1 to about 1 g. per square inch of layer into the absorbent article, the absorbent article comprising a liquid permeable cover and an absorbent core, wherein the odor control additive is a water soluble salt containing an anion selected from the group consisting of $P_3O_9^{3-}$ and $P_3O_{10}^{5-}$ and a cation containing a Group 1 element or ammonium.

10. The method of claim 9, wherein said Group 1 element is sodium.

11. The method of claim 9, wherein said odor control additive comprises pentasodium triphosphate.

12. A method of reducing malodors in a disposable, absorbent article, comprising incorporating into the absorbent article an odor control additive comprising a water soluble compound of the formula $(APO_3)_n$, wherein A is a Group 1 element and n is 4 to 50.

13. The method of claim g, wherein said Group 1 element is sodium, and n is 15 to 20.

14. A disposable, absorbent article of claim 1, wherein the amount of the odor control additive is from about 0.2 to about 0.5 g.

15. A method of reducing malodors in a disposable, absorbent article of claim 9, wherein the amount of odor control additive is from about 0.2 to about 0.5 g.

* * * * *